United States Patent [19]

Nelson

[11] 4,292,445

[45] Sep. 29, 1981

[54] AMIDE AND SULFONAMIDE DERIVATIVES OF 2-DECARBOXY-2-AMINOMETHYL-PG-TYPE COMPOUNDS

[75] Inventor: Norman A. Nelson, Charleston Township, Kalamazoo County, Mich.

[73] Assignee: The Upjohn Company, Kalamazoo, Mich.

[21] Appl. No.: 144,709

[22] Filed: Apr. 28, 1980

[51] Int. Cl.³ ............... C07C 103/00; C07C 143/72; A61K 31/16; A61K 31/18
[52] U.S. Cl. ............................................ 564/98; 564/92; 546/93; 564/96; 564/97; 564/99; 564/176; 564/185; 564/186; 564/210; 564/212; 564/217; 564/219; 424/320; 424/321; 424/324

[58] Field of Search ............... 564/89, 90, 92, 93, 564/96, 97, 98, 99, 167, 176, 182, 183, 185, 186, 187, 210, 212, 217, 219

[56] References Cited

U.S. PATENT DOCUMENTS

| | | | |
|---|---|---|---|
| 4,060,534 | 11/1977 | Bundy | 260/408 |
| 4,081,478 | 3/1978 | Nelson | 424/330 X |
| 4,171,331 | 10/1979 | Biddlecom et al. | 564/217 X |

*Primary Examiner*—Charles F. Warren
*Attorney, Agent, or Firm*—Lawrence T. Welch; Robert A. Armitage

[57] ABSTRACT

The present invention relates to novel amido and sulfonamido derivatives of 2-decarboxy-2-amino-methyl-PG-type compounds. These analogs are useful as nasal decongestants, antifertility agents, and as cytoprotection agents.

28 Claims, No Drawings 4,292,445

AMIDE AND SULFONAMIDE DERIVATIVES OF 2-DECARBOXY-2-AMINOMETHYL-PG-TYPE COMPOUNDS

DESCRIPTION

BACKGROUND OF THE INVENTION

The present invention relates to novel amide and sulfonamide derivatives of certain 2-decarboxy-2-aminomethyl-PG-type compounds. The free amine compounds from which the compounds of the present invention are derived are known in the art and are structural and pharmacological analogs of the prostaglandins.

The prostaglandins are a family of 20 carbon atom fatty acids, being structural derivatives of prostanoic acid, which exhibit useful activity in a wide variety of biological systems. Accordingly, such prostaglandins represent useful pharmacological agents in the treatment and prevention of a wide variety of disease conditions. The term "PG-type compounds" is used to describe structural analogs of the prostaglandins. For a fuller discussion of the prostaglandins, see Bergstrom, et al., Pharmacol. Rev. 20:1 (1968) and references cited therein.

Similarly, the 2-decarboxy-2-amino-methyl-PG-type compounds from which the compounds of the present invention are derived also exhibit useful activity in a wide variety of biological systems. They also represent useful pharmacological agents in the treatment and prevention of a wide variety of these disease conditions.

The compounds of the present invention are useful as nasal decongestants, antifertility agents, and as cytoprotection agents.

Prior Art

The known 2-decarboxy-2-amino-methyl-PG-type compounds are disclosed in U.S. Pat. Nos. 4,081,478 and 4,060,534.

SUMMARY OF THE INVENTION

The present invention comprises a prostaglandin analog of the formula I (a) wherein $R_8$ is hydrogen or hydroxy, (b) wherein $L_1$ is $\beta$—$R_3$:$\alpha$—$R_4$, $\alpha$—$R_3$: $\beta$—$R_4$ or a mixture of both, (c) wherein $R_3$ and $R_4$ are hydrogen, methyl, or fluoro, being the same or different, with the proviso that one of $R_3$ and $R_4$ is methyl only when the other is hydrogen or methyl;

(d) wherein $X_1$ is —CO—$R_1$ or —SO$_2$—$R_1$, wherein $R_1$ is alkyl of from 1 to 4 carbon atoms, —CH$_2$F, —CHF$_2$, —CF$_3$, phenyl, or monosubstituted phenyl, said substituted phenyl substituted by fluorine, chlorine, bromine, —CF$_3$, or —OCH$_3$ in the ortho, meta or para position, (e) wherein $M_1$ is $\alpha$—$R_5$:$\beta$—OH or $\beta$—$R_5$: $\alpha$—OH, wherein $R_5$ is hydrogen or methyl;

(f) wherein $W_1$ is $\alpha$—OH:$\beta$—H, $\alpha$—H:$\beta$—OH, oxo, or methylene;

(g) wherein $R_7$ is (1) —(CH$_2$)$_m$—CH$_3$, (2) —cis—CH=CH—CH$_2$CH$_3$, (3) phenyl or alkylphenyl, wherein the alkyl portion of the moiety is from one to 3 carbon atoms, and the phenyl portion is optionally substituted by one to 3 of the following: chloro, fluoro, trifluoromethyl, alkyl of from one to 3 carbon atoms, or alkoxy of from one to 3 carbon atoms, with the proviso that no more than 2 groups are other than alkyl; or (4) phenoxy optionally substituted by one, 2 or 3 of the following: chloro, fluoro, trifluoromethyl, alkyl of from one to 3 carbon atoms, or alkoxy of from one to 3 carbon atoms; with the proviso that no more than 2 groups are other than alkyl, wherein m is one to 5, inclusive;

(h) wherein $Y_1$ is (1) trans—CH=CH—, (2) cis—CH=CH—, (3) —CH$_2$CH$_2$—, or (4) —C≡C—; and (i) wherein $Z_1$ is (1) cis—CH=CH—CH$_2$—(CH$_2$)$_g$—CH$_2$—, (2) cis—CH=CH—CH$_2$—(CH$_2$)$_g$—CF$_2$—, (3) cis—CH$_2$—CH=CH—(CH$_2$)$_g$—CH$_2$, (4) —(CH$_2$)$_3$—(CH$_2$)$_g$—CH$_2$—.

(5) —(CH$_2$)$_3$—(CH$_2$)$_g$—CF$_2$—, (6) —CH$_2$—O—CH$_2$—(CH$_2$)—CH$_2$—, (7) —(CH$_2$)$_2$—O—(CH$_2$)$_g$—CH$_2$—, (8) —(CH$_2$)$_3$—O—(CH$_2$)$_l$—, (9) —(m—Ph)—CH$_2$—(CH$_2$)—, wherein (m-Ph) is 1,3-phenylene, or

(10) —(m—Ph)—O—(CH$_2$)$_g$—wherein (m—Ph) is 1,3-phenylene;

wherein g is zero, one, two, or three; and l is one, two, or three and the pharmacologically acceptable salts thereof when $X_1$ is —SO$_2$R$_1$.

This invention also comprises a compound of the formula II (a) wherein $W_1$ is $\alpha$—OH:$\beta$—H, $\alpha$—H:$\beta$—OH, oxo, or methylene, (b) wherein $R_8$ is hydrogen or hydroxy, (c) wherein $Z_1$ is (1) cis—CH=CH—CH$_2$—(CH$_2$)$_g$—CH$_2$—, (2) cis—CH=CH—CH$_2$—(CH$_2$)$_g$—CF$_2$—, (3) cis—CH$_2$—(CH=CH—(CH$_2$)$_g$—CH$_2$, (4) —(CH$_2$)$_3$—(CH$_2$)$_g$—CH$_2$—.

(5) —(CH$_2$)$_3$—(CH$_2$)$_g$—CF$_2$—, (6) —CH$_2$—O—CH$_2$—(CH$_2$)—CH$_2$—, (7) —(CH$_2$)$_2$—O—(CH$_2$)$_g$—CH$_2$—, (8) —(CH$_2$)$_3$—O—(CH$_2$)$_l$—, (9) —(m—Ph)—CH$_2$—(CH$_2$)—, wherein (m-Ph) is 1,3-phenylene, or

(10) —(m—Ph)—O—(CH$_2$)$_g$—wherein (m—Ph) is 1,3-phenylene;

wherein g is zero, one, two, or three; and l is one, two, or three (d) wherein $Y_1$ is (1) trans—CH=CH—, (2) cis—CH=CH—, (3) —CH$_2$CH$_2$—, or (4) —C≡C—;

(e) wherein $X_1$ is —CO—$R_1$ or —SO$_2$—$R_1$, wherein $R_1$ is alkyl of from one to 4 carbon atoms, —CH$_2$F, —CHF$_2$, —CF$_3$, phenyl, or monosubstituted phenyl, said substituted phenyl substituted by fluorine, chlorine, bromine, —CF$_3$, or —OCH$_3$ in the ortho, meta or para position, (f) wherein $R_{17}$ is phenoxy optionally substituted by one, 2 or 3 of the following: chloro, fluoro, trifluoromethyl, alkyl of from one to 3 carbon atoms, or alkoxy of from one to 3 carbon atoms; with the proviso that no more than 2 groups are other than alkyl; and (g) wherein $L_1$ is $\beta$-$R_3$:$\alpha$—$R_4$, $\alpha$—$R_3$:$\beta$—$R_4$ or a mixture of both,
wherein $R_3$ and $R_4$ are hydrogen, methyl, or fluoro, being the same or different, with the proviso that one of $R_3$ and $R_4$ is methyl only when the other is hydrogen or methyl; and the pharmacologically acceptable salts thereof when $X_1$ is —$SO_2R_1$.

Examples of alkyl of one to 4 carbon atoms, inclusive, are methyl, ethyl, propyl, butyl, and isomeric forms thereof.

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of substituted phenyl groups where $R_7$ is phenyl, alkylphenyl and phenoxy are (o-, m-, or p-)tolyl, (o-, m-, p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-. m-, or p-trifluoromethylphenyl, (o-, m-, or p-)methoxyphenyl, (o-, m-, or p-)ethoxyphenyl, (4- or 5-)chloro-2-methoxyphenyl, and 2,4-dichloro (5- or 6-)methylphenyl.

Examples of monosubstituted phenyl within the scope of $R_1$ include p-fluorophenyl, o-fluorophenyl, m-fluorophenyl, p-bromophenyl, o-bromophenyl, m-bromophenyl, p-trifluoromethyl, o-trifluoromethylphenyl, m-trifluoromethylphenyl, p-methoxyphenyl, o-methoxyphenyl, and m-methoxyphenyl.

With regard to the divalent substituents described above (e.g., $W_1$, $L_1$, and $M_1$), these divalent radicals are defined as $\alpha$-$R_i$:$\beta$-$R_j$, wherein $R_i$ represents the substituent of the divalent moiety in the alpha configuration with respect to the ring and $R_j$ represents the substituent of the divalent moiety in the beta configuration with respect to the plane of the ring. Accordingly, when $M_1$ is defined as $\alpha$OH:$\beta$-H, the hydroxy of the $M_1$ moiety is in the alpha configuration, and the hydrogen substituent is in the beta configuration.

Pharmaceutically acceptable salts when $X_1$ is $SO_2R_1$ include the potassium, sodium and lithium salts of these compounds.

The novel prostaglandin analogs described in this specification are named as (a) PGE-type compounds when $W_1$ is oxo and $R_8$ is hydroxy;

(b) PGF$\alpha$-type compounds when $W_1$ is $\alpha$-OH:$\beta$-H and $R_8$ is hydroxy;

(c) PGF$\beta$-type compounds when $W_1$ is $\beta$-OH:$\alpha$-H and $R_8$ is hydroxy;

(d) 11-deoxy-PGF$_\alpha$-type compounds when $W_1$ is $\alpha$-OH:$\beta$-H and $R_8$ is H;

(e) 11-deoxy-PGF$\beta$-type compounds when $W_1$ is $\beta$-OH:$\alpha$-H and $R_8$ is H;

(f) 11-dideoxy-PGE-type compounds when $W_1$ is oxo and $R_8$ is H;

(g) 9,11-dideoxy-9-methylene-PGF-type compounds when $W_1$ is methylene and $R_8$ is H; and (h) 9-deoxy-9-methylene-PGF-type compounds when $W_1$ is methylene and $R_8$ is hydroxy.

The various cyclopentane ring structures described is subparagraphs (a) through (h) are illustrated in Chart E.

For a further discussion of prostaglandin nomenclature, see U.S. Pat. No. 4,081,478, and N. A. Nelson, Journal of Medicinal Chemistry, 17:911 (1974).

The prostaglandins analogs of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 to $\mu$g to about 500 $\mu$g per kg of body weight per minute, or in a total daily dose by injection or infusion in the range about 0.1 to about 20 mg per kg of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for the purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE and PGA compounds. The compounds of the present invention are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example, indomethacine, aspirin, or phenylbutazone is administered in any of the ways known in the art to alleviate an inflammatory condition, for example, in any dosage regimen and by any of the known routes of systemic administration.

The prostaglandin analog is administered along with the anti-inflammatory prostaglandin synthetase inhibitor either by the same route of administration or by a different route. For example, if the anti-inflammatory substance is being administered orally, the prostaglandin is also administered orally, by alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dose form.

The dosage regimen for the prostaglandin in accord with this treatment will depend upon a variety of factors, including the type, age, weight, sex, and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experienced the same adverse gastrointestinal effects when taking the substance. The gastrointestinal effects with frequently vary substantially in kind and degree. But it is within the skill of the attending physician or veterinarian to determine that administration of the anti-inflammatory substance is causing undesirable gastrointestinal effects in the human or animal subject and to prescribe an effective amount of prostaglandin to reduce and then substantially to eliminate those undesirable effects.

The prostaglandin analogs of this invention are useful in mammals, including humans, as nasal decongestants. They are used for this purpose in a dose range of about 10 µg to about 10 mg per ml of pharmacologically suitable liquid vehicle or as an aerosol spray, both for topical application.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range 0.01 mg to about 20 mg per kg of body weight of the female mammal, advantageously during a span of time starting approximately at the time of ovulation and ending approximately at the time of menses or just prior to menses. Intravaginal and intrauterine routes are alternate methods of administration. These compounds are further useful in domestic animals as an aid to estrus detection, and for regulation or synchronization of estrus. Domestic animals include horses, cattle, sheep, and swine. The regulation or synchronization of estrus allows for more effecient management of both conception and labor by enabling the herdsman to breed all his femals in short pre-defined intervals. This synchronization results in a higher percentage of live births than the percentage achieved by natural control. The prostaglandin analog is injected or applied in a feed at doses of 0.1-100 mg per animal and may be combined with other agents such as steroids. Dosing schedules will depend on the species treated. For example, mares are given the prostaglandin 5 to 8 days after ovulation and return to estrus. Cattle are treated at regular intervals over a 3 week period to advantageously bring all into estrus at the same time.

The novel prostaglandin analogs of this invention are administered in various ways for various purposes, e.g., intravenously, intramuscularly, subcutaneously, orally, intravaginally, rectally, buccally, sublingually, topically, and the form of sterile implants for prolonged action. For intravenous injection or infusion, sterile aqueous isotonic solutions are preferred. For subcutaneous or intramuscular injection, sterile solutions or suspensions are used. Tablets, capsules, and liquid preparations such as syrups, elixirs, and simple solutions with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The PGF-type compounds of the present invention (i.e., where $W_1$ is not oxo) are prepared according to Chart A. A compound of the formula X, wherein $W_2$ is α—OH:β—H, α—H:β—OH, or methylene and all other variables are defined as above, is reacted with an appropriate sulfonylating agent of the formula $R_1$—$SO_2$—Cl or acylating agent of the formula $(R_1CO)_2$—O, or $R_1COCl$ wherein $R_1$ is defined as above, in a solvent such as methanol, tetrahydrofuran, or methylene chloride, to form a compound of formula XI.

As this reaction proceeds, an acid is liberated. If a strong acid is released, it is necessary to add an acid "scavenger", that is, a compound which neutralizes the strong acid. This scavenger is preferably a trialkylamine, triaralkylamine or similar tertiary amine. Suitable amines of this type include trimethylamine, triethylamine, tripropylamine, and tribenzylamine. It is preferred that the sulfonylations be conducted at −20° to 25° C., while acylations be conducted at 0° to 50° C.

The PGE-type compounds of the present invention are prepared according to Chart B. A compound of the formula XX, wherein $W_3$ is α—Oh:β—OH, or α—H:β—OH and $R_{10}$ is hydrogen or, —O—$R_{18}$, $M_2$ is α—$R_3$:β—O—$R_{18}$ or β—$R_3$:α—O—$R_{18}$, $R_{18}$ is a protective blocking group and all other variables are defined as above is allowed to react with isobutyl chloroformate (or a similar alkyl chloroformate) in the presence of a trialkylamine in a solvent such as tetrahydrofuran and the resulting mixed anhydride is treated with ammonia to form a compound of formula XXI. This compound is then reduced with an appropriate metal hydride in a solvent such as tetrahydrofuran, to form a compound of formula XXII. This compound is then sulfonylated or acylated according to the process of Chart A to form a compound of formula XXIII. The hydroxy substituent at $W_3$ is then oxidized by methods well known in the art, using an oxidation agent such as Jones reagent or Collins reagent, to form a compound of formula XXIV. The protective groups are removed by acid hydrolysis, using an organic acid such as acetic acid to form a compound of formula XXV.

The processes illustrated in Charts A and B are the preferred means of preparing the Formula I compounds of this invention.

Alternatively, the compounds are prepared according to the process of Chart C. A compound of formula XXX, with all variables defined as above, is reacted with diazomethane in ether to form a compound of formula XXXI. This compound is then reacted with a silylating agent to form a compound of formula XXXII, wherein $W_4$ is β—OH:α-O—$Si(G_1)_3$ or α—H:β—O—$Si(G_1)_3$ and —$Si(G_1)_3$ is a silyl protecting group. This compound is then reduced with an appropriate metal hydride to form a compound of formula XXXIII. This compound is then reacted with a sulfonyl chloride of formula $R_{50}$—$SO_2$—Cl, wherein $R_{50}$ is alkyl of from one to 12 carbon atoms, aryl of from 6–10 carbon atoms, aryl substituted by one to 3 substituents selected from methyl, fluorine, chlorine, or bromine, in pyridine to form a compound of formula XXXIV. This compound is then reacted with the sodium salt of the appropriate sulfonamide of the formula $R_1$—$SO_2$—$NH_2$ where $R_1$ is defined as above, to form a compound of formula XXXV. The silyl protecting group is removed by methods well known in the art to form a compound of the formula XXXVI. By proceeding in the manner given in Chart B, compounds of the invention wherein $W_1$ is oxo are prepared. Alternatively, the remaining blocking groups can be removed by acid hydrolysis without oxidation to produce a compound of the formula XXXVII. Using the process illustrated in Chart C, all of the sulfonamide compounds of this invention are prepared except those wherein $W_1$ is methylene.

As can be seen, this process involves several more steps than the processes of Charts A and B. However, compounds of the formula XXXIV are known and are described in U.S. Pat. No. 4,081,478. Thus, starting with this compound, the sulfonamide compounds of this invention (except where $W_1$ is methylene) are prepared in a three or four step process. Since all compounds represented by formula XXXIV are not readily available, it is preferred to use the processes illustrated in Charts A and B.

PGE-type compounds of the formula II, wherein $W_1$ is oxo, are formed during the oxidation steps of the processes of Charts B and C. See, e.g., Examples 3 and 4. More direct methods for preparing compounds of the formula II are depicted in Chart D.

In Chart D, a prostaglandin analog of the formula XL, wherein $M_3$ is $\alpha$—OH:$\beta$—H or $\alpha$—H:$\beta$—OH and all other variables are defined as above, is dissolved in a solvent such as methylene chlorine, chloroform, ethyl acetate, tetrahydrofuran, benzene, or the like, and is stirred with activated manganese dioxide for about 5 hr to form a compound of formula XLI.

Alternatively, in Chart D, the prostaglandin analog of the formula XL, is mixed with 1,4-dioxane and 850 mg of 2,3-dichloro-5,6-dicyano-1,4-benzoquinone (DDQ). The mixture is stirred at ambient temperature under nitrogen for about 72 hours to yield a compound of the formula XLI.

These synthetic procedures are described more fully below.

The protective groups within the scope of $R_{18}$ are any group which replaces a hydroxy hydrogen and is neither attacked by nor is as reactive to the reagents used in the transformations used herein as a hydroxy is and which is subsequently replaceable by acid hydrolysis with hydrogen in the preparation of the prostaglandin-type compounds. Several such protective groups are known in the art, e.g., tetrahydropyranyl and substituted tetrahydropropranyl. See for reference E. J. Corey, Proceedings of the Robert A. Welch Foundation Conferences on Chemical Research, XII Organic Synthesis, pgs. 51–79 (1969). Those blocking groups which have been found useful include:

(a) tetrahydropyranyl;
(b) tetrahydrofuranyl; and
(c) a group of the formula —C(OR$_{11}$)R$_{12}$)—CH(R$_{13}$)(R$_{14}$), wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted withy one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together —(CH$_2$)$_a$— or when $R_{12}$ and $R_{13}$ are taken together —(CH$_2$)$_b$—O—(CH$_2$)$_c$, wherein a is 3, 4, or 5 and b is one, 2 or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking groups $R_{10}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stiochiometric amount. The reaction is normally complete in less than an hour at 20°–50° C.

When the protective group is tetrahydrofuranyl, 2,3-dihydrofuran is used, as described in the preceding paragraph, in place of the 2,3-dihydropyran.

When the protective group is of the formula —C(OR$_{11}$)(R$_{12}$)—CH—(R$_{13}$)(R$_{14}$), wherein $R_{11}$, $R_{12}$, $R_{13}$, and $R_{14}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., Journal of the Chemical Society 86, 3366 (1967). The reaction conditions for such vinyl ethers and unsaturated compounds are similar to those for dihydropyran above.

As noted, $W_4$ contains a silyl protecting group of the formula —Si(G$_1$)$_3$. $G_1$ is alkyl of one to 4 carbon atoms, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, with the proviso that in a —Si(G$_1$)$_3$ moiety the various G$_1$'s are the same or different and at least one $G_1$ is hindered (such as tert-butyl). Silyl groups within the scope of —Si(G$_1$)$_3$ include dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-;b 2-methylphenyl, and 2,4-dichloro-3-methylphenyl. Tert-butyldimethylsilyl is most preferred as a silylating agent.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography is to be avoided. Further, when silyl groups are to be introduced selectively, silylating agents which are readily available and known to be usef in selective silylations are employed. For example, triphenylsilyl and t-butyldimethylsilyl groups are employed when selective introduction is required. Further, when silyl groups are to be selectively hydrolyzed in the presence of protective groups according to $R_{10}$ or acyl protective groups, then the use of silyl groups which are readily available and known to be easily hydrolyzable with tetra-n-butylammonium fluoride are employed. A particularly useful silyl group for this purpose is t-butyldimethylsilyl, although other silyl groups are likewise employed.

The protective groups as defined by $R_{10}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

The oxidating agents used in Chart B are Jones reagent (acidified chromic acid, see Journal of American Chemical Society 39 (1946)), Collins Reagent (Chrominium trioxide—pyridine complex, see Collins, et al., Tetrahedron Lett., 3363 (1968)), mixtures of chromium trioxide in pyridine (see Journal of American Chemical Society 75, 422 (1953)), tert-butyl chromate in pyridine (see Biological Chemistry Journal, 84 195 (1962)), mixtures of sulfur trioxide in pyridine and dimethyl sulfoxide (see Journal of the American Chemical Society 89, 5505 (1967)), and mixtures of dicyclohexylcarbodiimide and dimethylsulfoxide (see Journal of the American Chemical Society 87, 5661 (1965)). For a further discussion of this oxidation-step, see, e.g., U.S. Pat. Nos. 4,028,419, cols. 57–58.

The 2-decarboxy-2-amino-methyl-PG-type compounds from which the compounds of the present invention are derived are unstable in air as they tend to react with atmospheric carbon dioxide. This makes it difficult to formulate these compounds into pharmaceutically acceptable compositions. Even when formulated, they tend to have a short shelf life, as they tend to darken and change color on exposure to air. The compounds of the present invention are surprisingly and unexpectedly, more stable in air have a longer shelf life and are easier to formulate than the prior art compounds.

To obtain the optimum combination of biological response specificity, potency, and duration of activity, certain compounds within the scope of this invention are preferred as discussed below.

Especially preferred are those compounds which satisfy two or more of the preferences herein. Further, the preferences herein are expressly intended to describe the preferred compounds within the scope of any generic formula of novel prostaglandin analogs disclosed herein.

The PGE compounds of the present invention, wherein $W_1$ is oxo, are considerably more stable than the free bases from which they are derived. The terminal amino groups of the prior art PGE compounds readily react with the keto functions in both intra- and intermolecular reactions, making the compound inherently unstable. The PGE compounds of the present invention are surprisingly and unexpectedly more stable than the free bases from which they are derived. Thus, the PGE compounds of the present invention are particularly preferred.

Generally, however, where subgeneric grouping of PG analogs of any cyclopentane ring structure are described herein, then the corresponding subgeneric groupings of PG analogs of each of the remaining cyclopentane ring structures are intended to represent equally preferred embodiments of the present invention.

It is preferred that in the amide or sulfonamide terminated side chain, g be one or 3; it is especially preferred that g be one, i.e., the chain is the natural chain length of the prostaglandins. Further when $R_7$ is $-(CH_2)_m-CH_3$, it is preferred that m be 3 to 5. It is especially preferred that m be 3. For those compounds wherein $R_7$ is alkylphenyl it is preferred that the alkyl portion of the moiety is methylene, and when $R_7$ is phenyl, alkylphenyl, or phenoxy, it is preferred that the aryl portion of the moiety be unsubstituted or substituted by only one of chlorine, fluorine, or trifluoromethyl.

For those compounds wherein at least one of $R_3$ and $R^4$ is methyl or fluoro, it is preferred that $R^5$ be hydrogen. For those compounds wherein $R_5$ is methyl, it is preferred that $R_3$ and $R_4$ both be hydrogen. For those compounds wherein $R^7$ is phenyl, alkylphenyl or phenoxy it is preferred that $R_3$ and $R_4$ be hydrogen.

It is further preferred that the 15-hydroxyl be of the natural configuration.

DESCRIPTION OF THE PREFERRED EMBODIMENTS

This invention can be more fully understood by the examples given below.

EXAMPLE 1:

(15R)-2-Aminomethyl-2-decarboxy-16-phenoxy-17,18,19,20-tetranor-PGF$_2\alpha$, N-methanesulfonyl (Formula I: $X_1$ is $-SO_2CH_3$, $W_1$ is $\alpha$-OH:$\beta$-H, $R_8$ is hydroxy, $Y_1$ is trans—CH═CH—, $Z_1$ is cis—CH═CH—(CH$_2$)$_3$—, $M_1$ is $\alpha$-OH:$\beta$-H, $R_3$ and $R_4$ are hydrogen, and $R_7$ is phenoxy).

Refer to Chart A.

To a mixture of 150 mg of (15R)-2-aminomethyl-2-decarboxy-16-phenoxy-17,18,19,20-tetranor-PGF$_2\alpha$ and 3 ml of anhydrous methanol at 0° is added with stirring 5 drops of methanesulfonyl choride followed by 3 drops of triethylamine. The additions of methanesulfonyl chloride and triethylamine are repeated at 5-min intervals two times and after a total reaction time of 15 min, 1 g of ice and 6 drops of triethylamine are added. The mixture is stirred at room temperature for 30 min and is then concentrated in vacuo to remove most of the methanol. The residue is shaken with 50 ml of ethyl acetate and 20 ml of saturated brine containing 20 drops of concentrated hydrochloric acid. The organic layer is washed with saturated brine, dried and concentrated to give 130 mg of residue. The residue is chromatographed in a dry-packed column of 20 g of 63–200 $\mu$l silica gel (E. Merck) deactivated with 2 ml each of methanol and methylene chloride. The column is eluted with 12:88 methanol-methylene chloride and 2-ml fractions are collected. Fractions 12–20 yield 35 mg of desired product as a viscous residue. TLC (Silica gel): Rf≃0.61 in 15:85 methanol-methylene chloride. The Mass Spectrum shows a mixture of tris- and tetra-TMS derivatives was obtained. No M+ peaks were found. For the M+—CH$_2$OC$_6$H$_5$ ion of the tetra-TMS derivative: Calcd. for C$_{28}$H$_6$NO$_5$SSi$_4$: 634.3269. Found: 634.3275.

EXAMPLE 2:

(15R)-2-Aminomethyl-2-decarboxy-16-phenoxy-17,18,19,20-tetranor-PGF$_2\alpha$, N-acetyl (Formula I, $X_1$ is $-CO_2-CH_3$, $W_1$ is $\alpha-OH$:$\beta-H$, $R_8$ is hydroxy, $Y_1$ is trans—CH═CH—, $Z_1$ is cis—CH═CH—(CH$_2$)$_3$—, $M_1$ is $\alpha-OH$:$\beta-H$, $R_3$ and $R_4$ are hydogen, and $R_7$ is phenoxy).

Refer to Chart A.

To a mixture of 100 mg of (15R)-2-aminomethyl-2-decarboxy-16-phenoxy-17,18,19,20-tetranor-PGF$_2\alpha$ and 2 ml of anhydrous methanol at 25° is added with stirring 4 drops of acetic anhydride. The reaction is followed by TLC on silica gel plates with methanol containing 1% concentrated ammonium hydroxide. The reaction is complete within 5 min. Ice (1 g) and 4 drops of pyridine are added and, after stirring the mixture for 5 min, it is shaken with 50 ml of ethyl acetate and 20 ml of saturated brine containing 5 drops of concentrated hydrochloric acid. The organic layer is washed with saturated brine, dried and concentrated to give 110 mg of residue.

The residue is chromatographed in a dry-packed column of 20 g of 63-200μ silica gel (E. Merck) deactivated with 2 ml of methanol and 2 ml of methylene chloride. The column is eluted with 15:85 methanol-methylene chloride and 2-ml fractions are collected. Fractions 20-32 yield 100 mg of desired product as a viscous residue. TLC (Silica gel): Rf≃0.51 in 15:85 methanol-methylene chloride. NMR (CDCl$_3$, δ): 6.81-7.28 (m, 5H), 6.19-6.40 (t, 1H), 5.60-5.73 (m, 2H), 5.28-5.49 (m, 2H) and 1.90 (s, 3H). Mass Spectrum: For tris-TMS derivative: Calcd. for $C_{33}H_{39}NO_5Si_3$: 633.3701. Found: no M+ peak, weak M+—$CH_3$ peak at 618 and M+—$CH_2OC_6H_5$ at 526.3175 (Calcd: 526.3204). An appreciable amount of the tetra TMS derivative is also formed.

EXAMPLE 3:

(15R)-2-Aminomethyl-2-decarboxy-16-phenoxy-17,18,19,20-tetranor-PGE$_2$, N-acetyl (Formula I, $X_1$ is —$CO_2CH_3$, $W_1$ is oxo, $R_8$ is hydroxy, $Y_1$ is trans—CH=CH—, $Z_1$ is cis-CH=CH—$(CH_2)_3$—, $M_1$ is α—OH:β—H, $R_3$ and $R_4$ are hydrogen, and $R_7$ is phenoxy), and 2-Aminomethyl-2-decarboxy-15-dehydro-16-phenoxy-17,18,19,20-tetranor-PGE$_2$, N-acetyl (Formula II, $X_1$ is —$CO_2CH_3$, $W_1$ is oxo, $R_8$ is hydroxy, $Y_1$ is trans-CH=CH—, $Z_1$ is cis—CH=CH—$(CH_2)_3$—, $R_3$ and $R_4$ are hydrogen, and $R_{17}$ is phenoxy)

Refer to Chart B.

(a) (15R)-16-Phenoxy-17,18,19,20-tetranor-PGF$_{2α}$, amide, 11,15-bis(tetrahydropyranyl ether)

(15R)16-Phenoxy-17,18,19,20-tetranor-PGF$_{2α}$, 11,15-bis(tetrahydropyranyl ether), 4.0 g, is dissolved in 65 ml tetrahydrofuran, 5.8 ml water and 1.14 g (1.57 ml) triethylamine and cooled to 0°. Isobutylchloroformate, 1.53 g, (1.46 ml) is added slowly over a period of 5 minutes and stirred 25 minutes at 0° C. An excess of liquid ammonia is added and the reaction mixture is stirred for 3 hours at 0° C. The mixture is then concentrated at reduced pressure from a water bath (28° C.) and the residue is taken up in 125 ml of ethyl acetate and 7.5 ml of ethanol. The mixture is dried over anhydrous magnesium sulfate and concentrated in vacuo. The residue is "purged" by the addition of toluene and removing the solvent at approximately 1 torr to yield 5.5 g. The NMR spectrum (CDCl$_3$, δ) exhibits the following absorptions: multiplet 7.45 to 6.85 (5H), broad, 6.06 (2H), multiplet 5.87 to 5.13 (4H), broad singlet, 4.68 (2H), triplet 4.13, 4.05, 3.95 (2H). The product is used directly for Part b.

(b) (15R)-2-Aminomethyl-2-decarboxy-16-phenoxy-17,18,19,20-tetranor-PGF$_{2α}$, 11,15-bis(tetrahydropyranyl ether)

(15R)-16-Phenoxy-17,18,19,20-tetranor-PGF$_{2α}$, amide, 11,15-bis(tetrahydropyranyl ether), 5.5 g, is dissolved in 50 ml of tetrahydrofuran and added to a suspension of 5.0 g of lithium aluminum hydride in 450 ml of dry tetrahydrofuran. The reaction mixture is warmed to 65° C. and stirred overnight under a nitrogen atmosphere at that temperature. The reaction mixture is cooled to 0° C. and a mixture of 5 ml of water and 40 ml of tetrahydrofuran is added cautiously, followed by 20 ml of 10% sodium hydroxide solution. The mixture is stirred a few minutes and filtered by suction on a Buchner funnel. The residue is washed well with tetrahydrofuran and the combined organic phase is concentrated at reduced pressure to afford approximately 4 g of crude product. This material is examined by TLC on a silica gel plate developed in 20% methanol, 79% methylene chloride, 1% concentrated ammonium hydroxide. The developed plate indicates a major product Rf 0.30 and 3 minor less polar impurities and 1 minor more polar impurity. The crude product is chromatographed over 400 g of E. Merck #7734 silica gel which has been partially deactivated with a mixture of 6 ml of water and 30 ml of 5% concentrated ammonium hydroxide in methanol. The column is dry packed and wetted with 10% methanol, 89% methylene chloride and 1% ammonium hydroxide. The column is then eluted in 3 ml fractions with the following solvent mixtures:

200 ml-10% methanol, 89% methylene chloride, 1% NH$_4$OH;
800 ml-20% methanol, 79% methylene chloride, 1% NH$_4$OH;
800 ml-40% methanol, 59% methylene chloride, 1% NH$_4$OH;
800 ml-40% methanol, 39% methylene chloride, 1% NH$_4$OH;
400 ml-80% methanol, 19% methylene chloride, 1% NH$_4$OH.

The desired product is isolated in fractions 81 to 97, inclusive, and upon concentration at reduced pressure, yields 2.91 g. In the NMR spectrum (CDCl$_3$, δ), the following absorptions are observed; multiplet, 743 to 6.83 (5H); complex multiplet 5.80 to 5.26 (4H); broad singlet, 4.68 (2H); triplet, 4.11, 4.05, 3.95 (2H).

(c) (15R)-2-Aminomethyl-2-decarboxy-16-phenoxy-17,18,19,20-tetranor-PGF$_{2α}$, N-acetyl, 11,15-bis(tetrahydropyranyl ether)

(15R)-2-Aminomethyl-2-decarboxy-16-phenoxy-17,18,19,20-tetranor-PGF$_{2α}$, 11,15-bis(tetrahydropyranyl ether), 2.0 g, is dissolved in 20 ml of anhydrous methanol and 1 ml of acetic anhydride is added. The reaction mixture is stirred at room temperature for 5 minutes and the excess acetic anhydride is decomposed by the addition of 10 g of ice and 1.1 ml of pyridine. The mixture is stirred for 7 minutes and diluted with ethyl acetate. The organic phase is washed with ice cold dilute hydrochloric acid and 5 times with saturated brine before drying over magnesium sulfate. The extract is concentrated at reduced pressure to yield 2.2 g. TLC on a silica gel plate developed in 10% methanol, 89% methylene chloride and 1% conc. ammonium hydroxide indicates the product to be a single entity, Rf 0.79 as compared Rf 0.3 for the starting material. In the NMR spectrum (CDCl$_3$, δ), the following absorptions are observed: multiplet, 745 to 6.83 (5H); multiplet. 6.15 to 5.86 (1H); complex multiplet, 5.85 to 5.38 (4H); broad singlet, 4.68 (2H); triplet, 4.13, 4.03, 3.95 (2H); singlet, 1.93 (3H).

(d) (15R)-2-Aminomethyl-2-decarboxy-16-phenoxy-17,18,19,20-tetranor-PGE$_2$, N-acetyl and 2-Aminomethyl-2-decarboxy-15-dehydro-16-phenoxy-17,18,19,20-tetranor PGE$_2$, N-acetyl (15R)-2-Aminomethyl-2-decarboxy-16-phenoxy-17,18,19,20-tetranor-PGF$_{2α}$, N-acetyl, 11,15-bis(tetrahydropyranyl ether, 1.1 g is dissolved 25 ml of acetone and cooled to −15° C. with an ice methanol bath. Jones Reagent, 4 ml, is added dropwise over a period of 4 minutes and the reaction mixture is stirred at −15° C. to −10° C. for 30 minutes. The excess oxidant is decomposed by the addition of 5 ml of isopropyl alcohol and stirring at −10° C. for 5 minutes. The reaction mixture is diluted with ethyl acetate and washed with saturated saline 5 times to remove chromium salts. The organic extract is dried over anhydrous magnesium sulfate and concentrated in vacuo to yield approximately 1 g of residue. This material is taken up in 10 ml of acetic acid, 5 ml of water and 1 ml of tetrahydrofuran and warmed to 40° C. for 5 hours. The reaction mixture is diluted with saturated saline ad extracted with ethyl acetate. The extract is washed thoroughly with saturated saline, dried over anhydrous magnesium sulfate and concentrated in vacuo to afford 650 mg of crude product. This material is chromatographed over 70 g of E. Merck #7734 silica gel which has been partially deactivated with 7 ml of methanol and 7 ml of methylene chloride. The column is eluted in 10 ml fractions with 5% methanol in methylene chloride. Peaks of eluted material are detected in fractions 31 to 45, inclusive, (the Formula II Product) and 51 to 80, inclusive (the Formula I product). These materials are somewhat colored, yellow brown, and are rechromatographed as follows. The less polar entity, 90 mg, is rechromatographed over 20 g of E. Merck #7734, dry packed, wet with ethyl acetate. The column is eluted in 10 ml fractions with the following solvent mixtures:

100 ml ethyl acelate-100%
200 ml-5% methanol-95% ethyl acetate
200 ml-10% methanol-90% acetate.

Fractions 21 to 33 afford 2-Aminomethyl-2-decarboxy-15-dehydro-16-phenoxy-17,18,19,20-tetranor PGE$_2$, N-acetyl, 78 mg, a single entity by TLC on silica gel plates developed in a solvent system of 1% methanol in ethyl acetate shaken with water.

In the NMR spectrum (CDCl$_3$, δ), the following absorptions are observed: multiplet, 7.43 to 6.85 (7H) over-lapped with—multiplet, 6.93, 6.80, 6.38 (7H); broad multiplet, 6.22 to 5.96 (1H); multiplet, 5.45 to 5.13 (2H); singlet, 4.73 (2H); singlet, 1.92 (3H).

In the mass spectrum for the mono-TMS derivative, Found: 485.2628, Calculated for $C_{27}H_{39}SiNO_5$: 485.2597. This product is found in fractions 27 and 38 and on concentration yields 530 mg.

The more polar entity, fractions 51 to 80, affords the Formula I product, and is rechromatographed over 30 g of E. Merck #7734 silica gel, dry packed, wet with ethyl acetate. The column is eluted in 10 ml fractions with the following solvent mixtures:

100 ml—ethyl acetate
200 ml—5% ethanol—95% ethyl acetate
200 ml—10% methanol—90% ethyl acetate.

The product is isolated from fractions 37 to 48, inclusive, and afforded 232 mg. In the NMR spectrum (CDCl$_3$, δ), the following absorptions are observed: muliplet, 7.43 to 6.82 (5H); broad multiplet, 6.62 to 6.23 (1H); multiplets, 5.83 to 5.68 and 5.45 to 5.22 (2H); doublet, 4.0, 3.92 (2H); singlet, 1.9 (3H).

In the mass spectrum of the silylated derivative, Found: 559.3163, Calculated for $C_{30}H_{49}Si_2NO_5$: 559.3149. Ion peaks were observed at m/e 554, 469, 466, 452, 415, 376, 362, 308, 286. These data indicate the Formula I compound.

EXAMPLE 4:

(15R)-2-Aminomethyl-2-decarboxy-16-phenoxy-17,18,19,20-tetranor-PGE$_2$, N-methanesulfonyl (Formula I, $X_1$ is —SO$_2$, —CH$_3$, $W_1$ is oxo, $R_8$ is hydroxy, Y is trans-CH=CH—, $Z_1$ is cis—CH=CH—(CH$_2$)$_3$, $M_1$ is α—OH:β-H, $R_3$ and $R_4$ are hydrogen, and $R_7$ is phenoxy), and 2-Aminomethyl-2-decarboxy-15-dehydro-16-phenoxy-17,18,19,20-tetranor PGE$_2$, N-methanesulfonyl (Formula II, $X_1$ is —SO$_2$CH$_3$, $W_1$ is oxo, $R_8$ is hydroxy, $Y_1$ is trans-CH=CH—, $Z_1$ is cis—CH=CH—(CH$_2$)$_3$, $R_3$ and $R_4$ are hydrogen, and $R_{17}$ is phenoxy)

(a) (15R)-16-Phenoxy-17,18,19,20-tetranor-PGF$_{2\alpha}$, methyl ester, 11,15-bis(tetrahydropyranyl ether)

Refer to Chart C.

(15R)-16-Phenoxy-17,18,19,20-tetranor-PGF$_{2\alpha}$, 11,15-bis(tetrahydropyranyl ether) 2.6 g is dissolved in 100 ml of ether and treated with an excess of diazomethane in ether at room temperature for 30 minutes. The excess diazomethane and solvent are removed at reduced pressure and the residue affords 2.79 g. The product is compared by TLC with the starting free acid on a silica gel plate developed in 1 to 1 ethyl acetate-hexane containing 1% acetic acid. The acid shows a Rf 0.36 compared to Rf 0.64 (a single spot) for the ester. This material is used directly for step b.

(b) (15R)-16-Phenoxy-17,18,19,20-tetranor-PGF$_{2\alpha}$, 9-t-butyldimethylsilyl ether, 11,15-bis(tetrahydropyranyl ether)

(15R)-16-Phenoxy-17,18,19,20-tetranor-PGF$_{2\alpha}$, methyl ester, 11,15-bis(tetrahydropyranyl ether) 2.79 g is dissolved in 21 ml of dry dimethylformamide and cooled to 0° C. The solution is treated with a solution of 0.946 g of t-butyldimethylsilyl chloride and 0.86 g of imidazole in 21 ml of dimethylformamide for 40 minutes at 0° C. and at room temperature for 18 hours. The reaction mixture is poured into a mixture of saturated sodium chloride and sodium bicarbonate and extracted thoroughly with 4:1 hexane-ethyl acetate. The combined extract is washed successively with water, 0.5 M potassium bisulfate, water, saturated sodium bicarbonate, saturated sodium chloride and dried over anhydrous magnesium sulfate. The extract is concentrated in vacuo to afford 3.18 g of crude product. The material is purified by chromatography over 300 g of E. Merck #7734 silica gel, dry packed, and then wetted with 65% Skellysolve B (a commercial mixture of hexanes, B.P. 60°-68° C., essentially n-hexane)-35% ethyl acetate. The column is eluted in 20 ml fractions with 500 ml of the same solvent mixture followed by 500 ml of 50% Skellysolve B-50% ethyl acetate. The product is found as a single entity in fractions 38 to 54, inclusive, and is concentrated to afford 2.78 g. The infrared spectrum exhibited absorptions for carbonyl 1740 cm$^{-1}$; aromatic C=C 1515 cm$^{-1}$, 1500 cm$^{-1}$ and other strong absorptions at 1460 cm$^{-1}$, 1365 cm$^{-1}$, 1240 cm$^{-1}$, 1150 cm$^{-1}$, 1080 cm$^{-1}$, 1022 cm$^{-1}$, 930 cm$^{-1}$, 870 cm$^{-1}$, 840 cm$^{-1}$. There is no absorption for "OH". In the NMR spectrum, (CDCl$_3$, δ) the following pertinent absorptions are observed: complex multiplet, 741 to 6.80 (5H); complex multiplet, 5.81 to 5.15 (5H); broad singlet. 4.65 (2H); triplet, 4.10, 4.03, 3.96 (2H); singlet 9.90 (9H); singlet, 0.03 (6H); Ref TMS=0.

This product is used for step c.

(c) (15R)-16-Phenoxy-17,18,19,20-tetranor-5-cis, 13-trans-prostadiene-1,9α,11α,15-tetraol, 9-t-butyldimethylsilyl ether, 11,15-bis(tetrahydropyranyl ether)

A suspension of 1.5 g of lithium aluminum hydride in 100 ml of ether is prepared in a flask fitted with a dropping funnel, stirrer and nitrogen inlet. A solution of 2.87 g of (15R)-16-phenoxy-17,18,19,20-tetranor-PGF$_2\alpha$, methyl ester, 11,15-bis-(tetrahydropyranyl ether) in 50 ml of ether is added slowly and the reaction mixture is stirred at ambient temperature for 35 minutes. The excess reducing agent is decomposed by the cautious addition of 15 ml of ethyl acetate and 10 ml of water, respectively. The reaction mixture is stirred for 5 minutes and filtered by suction on a Buchner funnel. The residue is rinsed with ethyl acetate and the extract was concentrated at reduced pressure to afford 2.80 g. The product is compared to the starting ester by TLC on a silica gel plate developed in 2:1 cyclohexane-ethyl acetate. The Rf 0.5, for the product, a single entity, and Rf 0.8, for the starting material indicates the reduction to be complete. The infrared/CH$_2$Cl$_2$ spectrum exhibits the following absorptions: 3530 cm$^{-1}$, 1600 cm$^{-1}$, 1500 cm$^{-1}$, 1460 cm$^{-1}$, 1365 cm$^{-1}$, 1240 cm$^{-1}$, 1150 cm$^{-1}$, 1080 cm$^{-1}$, 1022 cm$^{-1}$, 930 cm$^{-1}$, 870 cm$^{-1}$ and 840 cm$^{-1}$.

This product is used for step d.

(d) (15R)-16-Phenoxy-17,18,19,20-tetranor-5-cis,13-trans-prostadiene-1,9$\alpha$,11$\alpha$,15-tetraol, 1-tosyl ester, 9-t-butyldimethylsilyl ether, 11,15-bis(tetrahydropyranyl ether) (15R)-16-Phenoxy-17,18,19,20-tetranor-5-cis, 13-trans-prostadiene-1,9$\alpha$,11$\alpha$,15-tetraol, 9-t-butyldimethylsilyl ether 11,15-bis(tetrahydropyranyl ether) 2.8 g is dissolved in 4 ml of pyridine and treated with 7.6 g tosyl chloride at room temperature overnight. The reaction mixture is poured into ice and water and stirred for 15 minutes. The mixture is acidified to pH 3 with ice cold dilute hydrochloric acid and extracted with ethyl acetate. The extract is washed with saturated sodium chloride, dried over anhydrous magnesium sulfate and concentrated in vacuo to afford appoximately 4.0 g of an oily product. The crude product is chroratographed over 400 g of E. Merck #7734 silica gel, dry packed, and then wetted with 20% ethyl acetate-80% Skellysolve B. The column is eluted in 35 ml fractions with the same solvent mixture. The product is found in fractions 25 to 40 and upon concentration, affords 2.4 g. The NMR spectrum (CDCl$_3$, $\delta$) shows the following absorptions: complex multiplets, 7.98 to 7.22 and 7.45 to 6.8 (9H); complex multiplets, 5.80 to singlet, 2.46 (3H); singlet, 0.88 (9H); singlet, 0.03 (6H); reference TMS 0.0.

This product is used for step c.

(e) (15R)-2-Aminomethyl-2-decarboxy-16-phenoxy-17,18,19,20-tetranor-PGF$_2\alpha$, N-methanesulfonyl, 9-t-butyldimethylsilyl ether, 11,15-bis(tetrahydropyranyl ether)

Methanesulfonamide, 4.7 g is dissolved in 13 ml of methanol and treated with 11.1 ml of 4.4 N-sodium methoxide in methanol. The reaction mixture is concentrated in vacuo and the residue, the sodium salt of methanesulfonamide is purged of any remaining methanol by twice adding benzene with subsequent reconcentration in vacuo. (15R)-16-Phenoxy-17,18,19,20-tetranor-5-cis, 13-trans-prostadiene-1,9$\alpha$,11$\alpha$,-15-tetraol, 1-tosyl ester, 9-t-butyldimethyldimethylsilyl ether, 11,15-bis(tetrahydropyranyl ether), 2.4 g. was dissolved in 40 ml of hexamethylphosphoramide and the sodium salt of the methane sulfonamide is added. The reaction mixture is stirred under nitrogen for 20 hours at room temperature, and protected from atmospheric moisture. The reaction mixture is poured into ice and water and acidified with ice cold dilute hydrochloric acid. The product is extracted with ethyl acetate and the organic phase is washed 5 times with saturated sodium chloride, dried over magnesium sulfate and concentrated at reduced pressure to afford 2.47 g of crude product. This material is purified by chromatography over 250 g of E. Merck #7734 silica gel, dry packed and then wet with 67% Skellysolve B and 33% ethyl acetate. The column is eluted in 20 ml fractions with the same solvent mixture (500 ml) followed by 500 ml of 1:1 Skellysolve B-ethyl acetate. The product is isolated from fractions 42 to 60, inclusive, and upon concentration affords 680 mg. In the NMR spectrum (CDCl$_3$, $\delta$), the following pertinent absorptions are observed: multiplet, 7.40 to 6.80 (5H); multiplet, 5.82 to 5.15 (4H); multiplet and broad singlet, 4.96 to 4.45 and 4.65 (3H), triplet, 4.1, 4.03, 3.93 (2H); singlet, 2.85 (3H); and singlet, 0.90 (9H).

This product is used for step f.

(f) (15R)-2-Aminomethyl-2-decarboxy-16-phenoxy-17,18,19,20-tetranor-PGF$_2\alpha$, N-methanesulfonyl, 11,15-bis(tetrahydropyranyl ether)

(15R)-2-Aminomethyl-2-decarboxy-16-phenoxy-17,18,19,20-tetranor-PGF$_2\alpha$, N-methanesulfonyl, 9-t-butyldimethylsilyl ether, 11,15-bis(tetrahydropyranyl ether), 680 mg, is dissolved in 100 ml of dry tetrahydrofuran stirred with 3 ml of 0.75 N tetrabutylammonium fluoride at room temperature for 18 hours. The mixture is poured into ice and water and extracted with ethyl acetate. The extract is washed 7 times with saturated brine solution, dried over anhydrous magnesium sulfate and concentrated to a syrup at reduced pressure. The residue, 580 mg, is examined by TLC on a silica gel plate developed in 1:1 ethyl acetate-cyclohexane, sprayed with vanillin-phosphoric acid reagent and heated. The TLC plate indicated a single entity, Rf 0.61. In the NMR spectrum (CDCl$_3$, $\delta$), the following absorptions are observed: multiplet, 7.40 to 6.85 (15H); multiplet, 5.85 to 5.30 (4H); broad singlet, 4.68 (2H); triplet, 4.12, 4.03, 3.96 (2H); singlet, 2.90 (3H).

This material is used directly for step g without further purification.

(g) (15R)-2-Aminomethyl-2-decarboxy-16-phenoxy-17,18,19,20-tetranor-PGE$_2$, N-methanesulfonyl and 2-Aminomethyl-2-decarboxy-15-dehydro-16-phenoxy-17,18,19,20-tetranor-PGE$_2$, N-methanesulfonyl (15R)-2-Aminomethyl-2-decarboxy-17,18,19,20-tetranor-PGF$_2\alpha$, N-methanesulfonyl, 11,15-bis(tetrahydropyranyl ether), 580 mg, is dissolved in 25 ml of acetone and cooled to $-15°$ C. with an ice-methanol bath. This solution is treated with 3.5 ml of Jones Reagent for 35 minutes at $-15°$ C. to $-10°$ C. The excess oxidant is decomposed by the addition of 3.5 ml of isopropyl alcohol followed by 5 minutes of stirring. The reaction mixture is poured into saturated sodium chloride and extracted with ethyl acetate. The extract is washed well with the saturated sodium chloride to remove chromium salts, dried over magnesium sulfate, and concentrated at reduced pressure to a yellow-brown syrup. The residue is taken up in 10 ml of acetic acid, 5 ml of water and 2 ml of tetrahydrofuran and warmed to 40° C. for 5 hours. The mixture is diluted with saturated sodium chloride and extracted with ethyl acetate. The extract is backwashed with saturated sodium chloride to remove acetic acid, dried over magnesium sulfate and concentrated in vacuo to afford 400 mg of crude product. This material is chromatographed over 40 g of E. Merck #7734 silica gel partially deactivated with 5 ml of methanol and 5 ml of methylene chloride. The column is eluted in 10 ml fractions with 5% methanol in methylene chloride. TLC on silica gel plates are developed in 10% methanol in methylene chloride and indicate the presence of two products. Fractions 10 to 18, comprise the first peak, RF 0.72, and afford 160 mg. Fractions 40 to 45 comprise the second peak, RF 0.63, and afford 100 mg. Both products are quite colored (yellowbrown) and it is necessary to rechromatograph both materials from E. Merck #7734 silica gel, dry packed, and then wetted with 75% ethyl acetate-25% hexane. The column (16 gm of silica gel) for the less polar entity is eluted in 5 ml fractions with the following solvent mixtures: 50 ml, 75% ethyl acetate-25% hexane 50 ml, 85% ethyl acetate-15% hexane 50 ml, 95% ethyl acetate-5% hexane 50 ml, 100% ethyl acetate.

Fractions 24 to 38 afford 88 mg of a pale yellow oil. In the NMR spectrum ($CHCl_3$, $\delta$), the following pertinent absorptions are observed: multiplet 7.45 to 6.83 (5H); multiplet, 6.66, 6.38, 5.78 overlapped with previous multiplet (2H); multiplet, 5.53 to 5.18 (2H); singlet, 4.75 (2H); singlet, 2.90 (3H).

In the infrared spectrum, absorptions are observed at 3340 $cm^{-1}$, 3200 $cm^{-1}$, 1730 $cm^{-1}$, 1675 $cm^{-1}$, 1602 $cm^{-1}$, 1580 $cm^{-1}$, 1470 $cm^{-1}$, 1310 $cm^{-1}$, 1210 $cm^{-1}$, 1140 $cm^{-1}$, 1070 $cm^{-1}$, and 965 $cm^{-1}$. In the mass spectrum, the silylated derivative appears to be di-TMS of the enol form, Found 593.2651, Calculated for $C_{29}H_{47}Si_2O_6SN$, 593.2662. These data would indicate this material to be (15R)-2-aminomethyl-2-decarboxy-15-dehydro-16-phenoxy-17,18,19,20-tetranor PGE$_2$, N-methanesulfonyl.

The more polar material is re-chromatographed over 10 gm of silica gel collecting 5 ml fractions eluted with the following solvent mixtures:

50 ml, 85% ethyl acetate-15% hexane,
50 ml, 95% ethyl acetate-5% hexane,
50 ml, 100% ethyl acetate,
50 ml, 1% methanol-99% ethyl acetate.

Fractions 52 to 70, containing a single entity, affords 92 mg of a pale yellow syrup. In the NMR spectrum ($CDCl_3$, $\delta$), the following pertinent absorptions are observed: multiplet 7.45 to 6.83 (5H); multiplet, 5.86 to 5.66 (2H); multiplet, 5.47 to 5.22 (2H); triplet, 4.11, 4.05, 3.95 (2H); singlet, 2.88 (3H). In the mass spectrum of the silylated derivative weak M+ and M+—$CH_3$ are observed at 595 and 580, respectively. M+—($C_2H_2OC_6H_5$), found: 488.2304; Calculated for $C_{22}H_{42}Si_2NO_5S$: 488.2322.

These data indicate the material to be the Formula I compound.

EXAMPLE 5:
2-Aminomethyl-2-decarboxy-15-dehydro-16-phenoxy-17,18,19,20-tetranor-PGE$_2$, N-methanesulfonyl (Formula II, $X_1$ is —$SO_2CH_3$, $R_8$ is hydroxy, $W_1$ is oxo, $Z_1$ is cis—CH=CH—($CH_2$)$_3$—, $R_3$ and $R_4$ are hydrogen, $R_{17}$ is phenoxy and $Y_1$ is trans—CH=CH—)

Refer to Chart D.

A mixture of 1.0 g of (15R) 2-aminomethyl-2-decarboxy-16-phenoxy-17,18,19,20-tetranor-PGE$_2$, N-methanesulfonyl, 30 ml of methylene chloride, and 10.0 g of activated manganese dioxide (Winthrop Laboratories) is stirred at ambient temperature for about 5 hr (the reaction is followed conveniently by thin layer chromatography on silica gel with ethyl acetate and, if necessary, additional activated manganese dioxide and solvent are added). The mixture is diluted with 50 ml of the reaction solvent and filtered through a pad of Celite. The solids are washed with 100 ml of solvent and the combined filtrate is concentrated in vacuo.

The residue is chromatographed (if necessary) in a column of 100 g of silica gel. The column is eluted with ethyl acetate (or other suitable solvent or solvent combination) and the fractions containing product free of impurities are combined and concentrated to give the desired product.

EXAMPLE 6:
2-Aminomethyl-2-decarboxy-15-dehydro-16-phenoxy-17,18,19,20-tetranor-PGF$_2\alpha$, N-acetyl (Formula II, $X_1$ is —$CO_2CH_3$, $R_8$ is hydroxy, $W_1$ is $\alpha$—OH:$\beta$-H, $Z_1$ is cis-CH=CH—($CH_2$)$_3$—, $R_3$ and $R_4$ are hydrogen, $R_{17}$ is phenoxy and $Y_1$ is trans—CH=CH—)

Refer to Chart D.

A mixture of 1.0 g of 2-aminomethyl-2-decarboxy-16-phenoxy-17,18,19,20-tetranor-PGF$_2\alpha$, N-acetyl, 30 ml of reagent grade 1,4-dioxane and 850 mg of 2,3-dichloro-5,6-dicyano-1,4-benzoquinone (DDQ) is stirred at ambient temperature under nitrogen for about 72 hr (the reaction is followed conveniently by thin layer chromatography on silica gel with ethyl acetate, if desirable, a shorter or longer reaction time may be used). The mixture is filtered through a pad of Celite and the solids are washed with methylene chloride. The combined filtrate is concentrated in vacuo and the residue is chromatographed in a column of 100 g of silica gel. The column is eluted with ethyl acetate (or other suitable solvent or solvent combination) and the fractions containing product free of impurities are combined and concentrated to give the desired product.

EXAMPLE 7

Following the procedure of Examples 1–6, N-methanesulfonyl and N-acetyl derivatives of PGE, PGF$\alpha$, PGF$\beta$, 11-deoxy-PGF$\alpha$, 11-deoxy-PGF$\beta$, 11-deoxy-PGE, 9,11-deoxy-9-methylene PGF and 9-deoxy-9-methylene PGF type compounds are prepared exhibiting the following side chain variations:

15-methyl-;
16-methyl-;
16,16-dimethyl-;
16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-trinor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
15-methyl-16-phenoxy-17,18,19,20-tetranor;
16-phenoxy-18,19,20-trinor-;
15-methyl-16-phenoxy-18,19,20-trinor-;
13,14-didehydro-;
15-methyl-13,14-didehydro-;
16-methyl-13,14-didehydro-;
16,16-dimethyl-13,14-didehydro-;
16-fluoro-13,14-didehydro-;

16,16-difluoro-13,14-didehydro-;
17-phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
15-methyl-16-phenoxy-17,18,19,20-tetranor-13,14-didehydro-;
16-phenoxy-18,19,20-trinor-13,14-didehydro-;
15-methyl-16-phenoxy-18,19,20-trinor-13,14-didehydro-;
16-methyl-16-phenoxy-18,19,20-trinor-13,14-didehydro-;
13,14-dihydro-;
15-,methyl-13,14-dihydro-;
16-methyl-13,14-dihydro-;
16,16-dimethyl-13,14-dihydro-;
16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro;
16-fluoro-17-phenyl-18,19,20-trinor-13,14-dihydro-;
16,16-difluoro-17-phenyl-18,19,20-trinor-13,14-dihydro-;
15-methyl-16,16-difluoro-17-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
15-dehydro-16-(m-trifluoromethylphenoxy)-17,18,19,20-tetranor-13,14-dihydro-;
15-dehydro-16-(m-chlorophenoxy)-17,18,19,20-tetranor-13,14-dihydro-;
15-dehydro-16-(p-fluorophenoxy)-17,18,19,20-tetranor-13,14-dihydro-;
15-dehydro-16-phenoxy-18,19,20-trinor-13,14-dihydro-;
15-dehydro-16-methyl-16-phenoxy-18,19,20-trinor-13,14-dihydro-;
15-dehydro-16-methyl-16-phenoxy-18,19,20-trinor-; and
15-dehydro-16,16-dimethyl-16-phenoxy-17,18,19,20-tetranor-13,14-dihydro-;

All the other compounds falling within the scope of this invention are prepared by these means.

FORMULAS

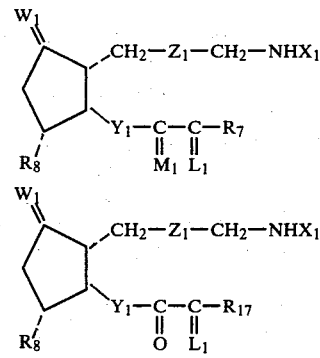

I

II

CHART A

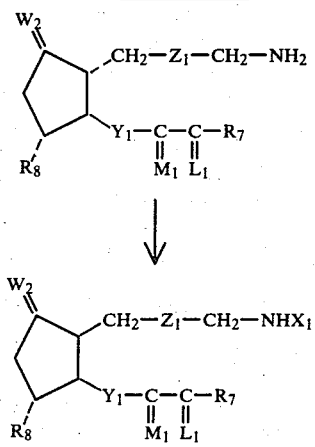

X

XI

CHART B

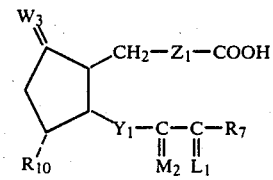

XX

-continued
CHART B
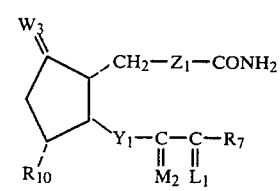
XXI
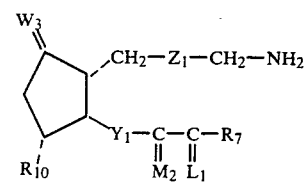
XXII
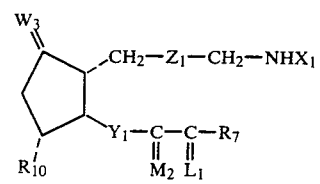
XXIII
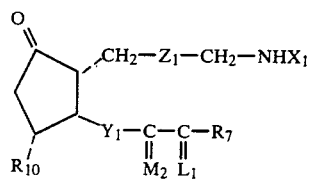
XXIV
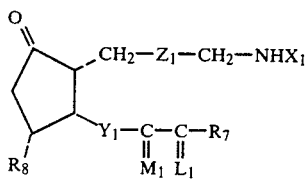
XXV
CHART C
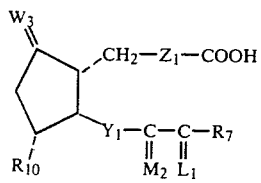
XXX
-continued
CHART C
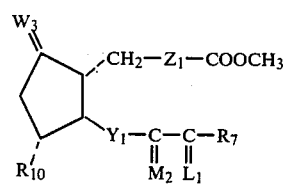
XXXI
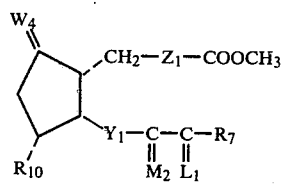
XXXII
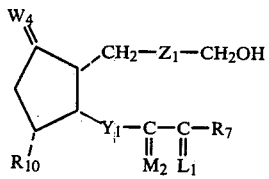
XXXIII
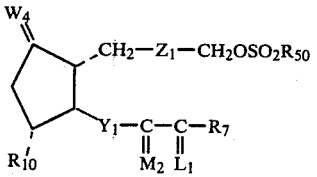
XXXIV
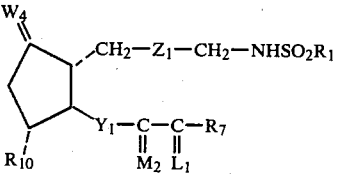
XXXV
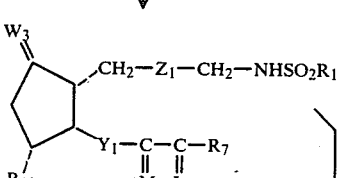
XXXVI

CHART C -continued

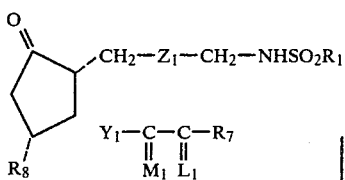

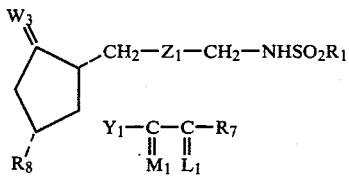

CHART D

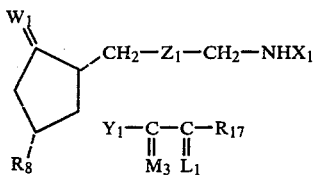

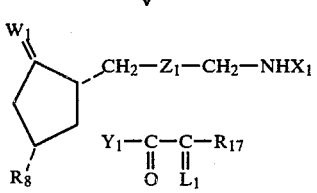

CHART E

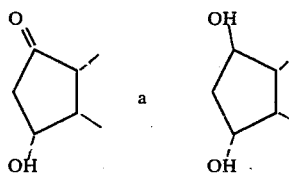 a 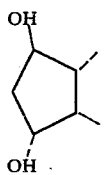 b

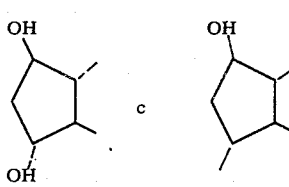 c 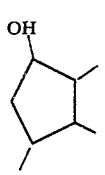 d

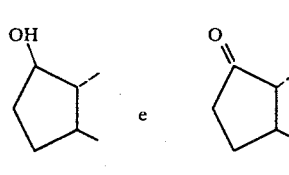 e 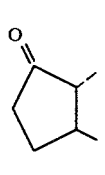 f

CHART E -continued

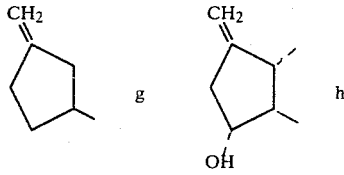 g 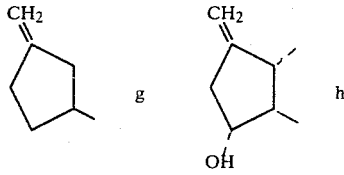 h

I claim:
1. A prostaglandin analog of the formula I

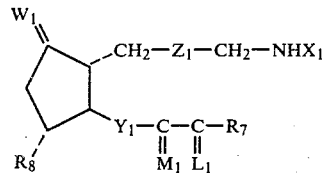

(a) wherein $R_8$ is hydrogen or hydroxy,
(b) wherein $L_1$ is $\beta$-$R_3$:$\alpha$-$R_4$, $\alpha$-$R_3$:$\beta$-$R_4$ or a mixture of both,
(c) wherein $R_3$ and $R_4$ are hydrogen, methyl, or fluoro, being the same or different, with the proviso that one of $R_3$ and $R_4$ is methyl only when the other is hydrogen or methyl;
(d) wherein $X_1$ is —CO—$R_1$ or $SO_2$—$R_1$, wherein $R_1$ is alkyl of from 1 to 4 carbon atoms, —$CH_2F$, —$CHF_2$, —$CF_3$, phenyl, or monosubstituted phenyl, said substituted phenyl substituted by fluorine, chlorine, bromine, —$CF_3$, or —$OCH_3$ in the ortho, meta or para position,
(e) wherein $M_1$ is $\alpha$-$R_5$:$\beta$-OH or $\beta$-$R_5$:$\alpha$-OH; wherein $R_5$ is hydrogen or methyl;
(f) wherein $W_1$ is $\alpha$-OH:$\beta$-H, $\alpha$-H:$\beta$-OH, oxo, or methylene;
(g) wherein $R_7$ is
(1) —$(CH_2)_m$—$CH_3$,
(2) -cis—CH=CH—$CH_2CH_3$,
(3) phenyl or alkylphenyl, wherein the alkyl portion of the moiety is from one to 3 carbon atoms, and the phenyl portion is optionally substituted by one to 3 of the following: chloro, fluoro, trifluoromethyl, alkyl of from one to 3 carbon atoms, with the proviso that no more than 2 groups are other than alkyl; or
(4) phenoxy optionally substituted by one, 2 or 3 of the following: chloro, fluoro, trifluoromethyl, alkyl of from one to 3 carbon atoms, or alkoxy of from one to 3 carbon atoms; with the proviso that no more than 2 groups are other than alkyl; wherein m is one to 5, inclusive,
(h) wherein $Y_1$ is
(1) trans—CH=CH—,
(2) cis—CH=CH—,
(3) —$CH_2CH_2$—, or
(4) —C≡C—; and
(i) wherein $Z_1$ is
(1) cis—CH=CH—$CH_2$—$(CH_2)_g$—$CH_2$—,
(2) cis—CH=CH—$CH_2$—$(CH_2)_g$—$CF_2$—,
(3) cis—$CH_2$—CH=CH—$(CH_2)_g$—$CH_2$,
(4) —$(CH_2)_3$—$(CH_2)_g$—$CH_2$—,
(5) —$(CH_2)_3$—$(CH_2)_g$—$CF_2$—,
(6) —$CH_2$—O—$CH_2$—$(CH_2)$—$CH_2$—,
(7) —$(CH_2)_2$—O—$(CH_2)_g$—$CH_2$—,
(8) —$(CH_2)_3$—O—$(CH_2)_{107}$—, (9) —(m-Ph)—CH$_2$—(CH$_2$)—, wherein (m-Ph) is 1,3-phenylene, or

(10) —(m-Ph)—O—(CH$_2$)$_g$— wherein (m-Ph) is 1,3-phenylene, wherein g is zero, one, two, or three and l is one, two or three; and the pharmacologically acceptable acid addition salts thereof when X$_1$ is —SO$_2$R$_1$.

2. A compound of claim 1 wherein W$_1$ is oxo and R$_8$ is H.

3. A compound of claim 1 wherein W$_1$ is methylene and R$_8$ is H.

4. A compound of claim 1 wherein W$_1$ is α-OH:β-H and R$_8$ is H.

5. A compound of claim 1 wherein W$_1$ is β-OH:α-H and R$_8$ is H.

6. A compound of claim 1 wherein W$_1$ is oxo and R$_8$ is OH.

7. A compound of claim 1 wherein W$_1$ is methylene and R$_8$ is —OH.

8. A compound of claim 1 wherein W$_1$ is β-OH:α-H and R$_8$ is —OH.

9. A compound of claim 1 wherein W$_1$ is α-OH:β-H and R$_8$ is —OH.

10. A compound of claim 1 wherein g is one.

11. A compound of claim 10 wherein R$_7$ is phenyl, alkylphenyl, or phenoxy and R$_3$ and R$_4$ are hydrogen.

12. A compound of claim 10 wherein R$_7$ is —(CH$_2$)$_3$—CH$_3$.

13. A compound of claim 1 wherein R$_1$ is alkyl of from 1-4 carbon atoms.

14. A compound of claim 11 wherein R$_1$ is methyl or ethyl.

15. A compound of claim 11 wherein the aryl groups are unsubstituted or monosubstituted by chloro, fluoro, or trifluoromethyl.

16. (15R)-2-Aminomethyl-2-decarboxy-16-phenoxy-17,18,19,20-tetranor-PGF$_2$α, N-acetyl, a compound of claim 1.

17. (15R)-2-Aminomethyl-2-decarboxy-16-phenoxy-17,18,19,20-tetranor-PGF$_2$α, N-methylsulfonyl, a compound of claim 1.

18. (15R)-2-Aminomethyl-2-decarboxy-16-phenoxy-17,18,19,20-tetranor-PGE$_2$, N-acetyl, a compound of claim 1.

19. (15R)-2-Aminomethyl-2-decarboxy-16-phenoxy-17,18,19,20-tetranor-PGE$_2$, N-methylsulfonyl, a compound of claim 1.

20. A compound of the formula II

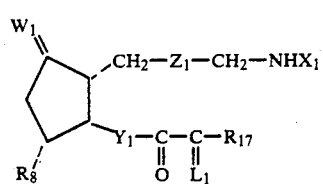

(a) wherein W$_1$ is α-OH:β-H, α-H:β-OH, oxo, or methylene, (b) wherein R$_8$ is hydrogen or hydroxy, (c) wherein Z$_1$ is (1) cis—CH=CH—CH$_2$—(CH$_2$)$_g$—CH$_2$—, (2) cis—CH=CH—CH$_2$—(CH$_2$)$_g$—CF$_2$—, (3) cis—CH$_2$—CH=CH—(CH$_2$)$_g$—CH$_2$, (4) —(CH$_2$)$_3$—(CH$_2$)$_g$—CH$_2$—, (5) —(CH$_2$)$_3$—(CH$_2$)$_g$—CF$_2$—, (6) —CH$_2$—O—CH$_2$—(CH$_2$)—CH$_2$—, (7) —(CH$_2$)$_2$—O—(CH$_2$)$_g$—CH$_2$—, (8) —(CH$_2$)$_3$—O—(CH$_2$)$_l$—, (9) —(m-Ph)—CH$_2$—(CH$_2$)—, wherein (m—Ph) is 1,3phenylene, or

(10) —(m-Ph)—O—(CH$_2$)$_g$— wherein (m-Ph) is 1,3-phenylene;

wherein g is zero, one, two, or three; and l is one, two, or three (d) wherein Y$_1$ is (1) trans—CH=CH—, (2) cis—CH=CH—, (3) —CH$_2$CH$_2$—, or (4) —C≡C—;

(e) wherein X$_1$ is —CO—R$_1$ or —SO$_2$—R$_1$, wherein R$_1$ is alkyl of from one to 4 carbon atoms, —CH$_2$F, —CHF$_2$, —CF$_3$, phenyl, or monosubstituted phenyl, said substituted phenyl substituted by fluorine, chlorine, bromine, —CF$_3$, or —OCH$_3$ in the ortho, meta or para position, (f) wherein R$_7$ is phenoxy optionally substituted by one, 2 or 3 of the following: chloro, fluoro, trifluoromethyl, alkyl of from one to 3 carbon atoms, or alkoxy of from one to 3 carbon atoms; with the proviso that no more than 2 groups are other than alkyl; and (g) wherein L$_1$ is β-R$_3$:α-R$_3$:β-R$_4$ or a mixture of both, wherein R$_3$ and R$_4$ are hydrogen, methyl, or fluoro, being the same or different, with the proviso that one of R$_3$ and R$_4$ is methyl only when the other is hydrogen or methyl; and the pharmacologically acceptable salts thereof when X$_1$ is —SO$_2$R$_1$.

21. (15R)-2-Aminomethyl-2-decarboxy-15-dehydro-16-phenoxy-17,18,19,20-tetranor-PGE$_2$, N-acetyl, a compound of claim 20.

22. (15R)-2-aminomethyl-2-decarboxy-15-dehydro-16-phenoxy-17,18,19,20-tetranor-PGE$_2$, N-methanesulfonyl, a compound of claim 20.

23. A compound of claim 1, wherein X$_1$ is —CO—R$_1$.

24. A compound of claim 1, wherein X$_1$ is —SO$_2$R$_1$.

25. A compound of claim 1, wherein R$_7$ is phenoxy optionally substituted by one, 2, or 3 of the following: chloro, fluoro, trifluoromethyl, alkyl of from one to 3 carbon atoms, or alkoxy of from one to 3 carbon atoms; with the proviso that no more than two groups are other than alkyl.

26. A compound of claim 20, wherein X$_1$ is —CO—R$_1$.

27. A compound of claim 20, wherein X$_1$ is —SO$_2$—R$_1$.

28. A compound of claim 20, wherein R$_7$ is phenoxy optionally substituted by one, 2, or 3 of the following: chloro, fluoro, trifluoromethyl, alkyl of from one to 3 carbon atoms, or alkoxy of from one to 3 carbon atoms; with the proviso that no more than two groups are other than alkyl.

* * * * *

UNITED STATES PATENT AND TRADEMARK OFFICE
CERTIFICATE OF CORRECTION

PATENT NO. : 4,292,445
DATED : 29 September 1981
INVENTOR(S) : Norman A. Nelson

It is certified that error appears in the above—identified patent and that said Letters Patent is hereby corrected as shown below:

Column 2, line 40, "(3) cis-CH$_2$-(CH=CH-..." should read -- (3) cis-CH$_2$-CH=CH-... --.

Column 3, line 49, "αOH:β-H," should read -- α-OH:β-H, --.

Column 7, line 27, "chlorine," should read -- chloride, --.

Column 20, line 25, the formula portion should appear as follows:

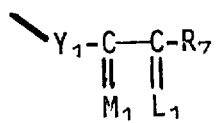

Column 20, line 33, the formula portion should appear as follows:

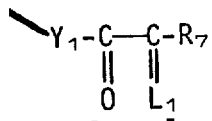

Column 20, line 43, the formula portion should appear as follows:

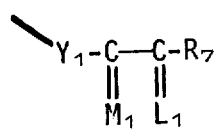

Column 20, line 53, the formula portion should appear as follows:

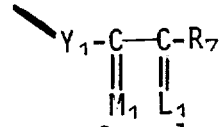

Column 20, line 63, the formula portion should appear as follows:

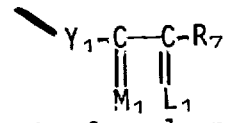

Column 21, line 9, the formula portion should appear as follows:

UNITED STATES PATENT OFFICE
CERTIFICATE OF CORRECTION

Patent No. 4,292,445  Dated 29 September 1981

Inventor(s) Norman A. Nelson

It is certified that error appears in the above-identified patent and that said Letters Patent are hereby corrected as shown below:

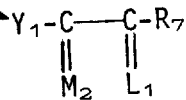

Column 21, line 20, the formula portion should appear as follows:

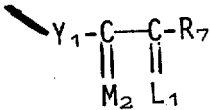

Column 21, line 28, the formula portion should appear as follows:

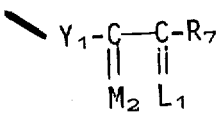

Column 21, line 50, the formula portion should appear as follows:

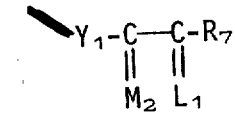

Column 21, line 62, the formula portion should appear as follows:

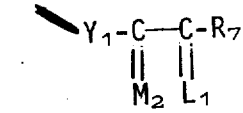

Column 22, line 8, the formula portion should appear as follows:

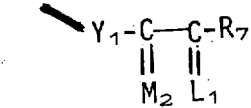

Column 22, line 19, the formula portion should appear as follows:

UNITED STATES PATENT OFFICE
CERTIFICATE OF CORRECTION

Page 3 of 5

Patent No. 4,292,445  Dated 29 September 1981

Inventor(s) Norman A. Nelson

It is certified that error appears in the above-identified patent and that said Letters Patent are hereby corrected as shown below:

Column 22, line 30, the formula portion should appear as follows:
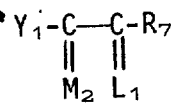

Column 22, line 41, the formula portion should appear as follows:
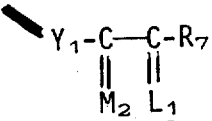

Column 22, line 52, the formula portion should appear as follows:
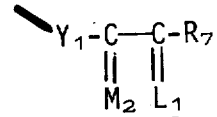

Column 22, line 63, the formula portion should appear as follows:
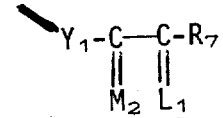

Column 23, line 8, the formula portion should appear as follows:
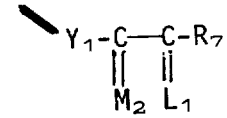

Column 23, line 17, the formula portion should appear as follows:
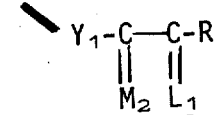

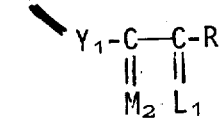

UNITED STATES PATENT OFFICE
CERTIFICATE OF CORRECTION

Patent No. 4,292,445        Dated  29 September 1981

Inventor(s)  Norman A. Nelson

It is certified that error appears in the above-identified patent and that said Letters Patent are hereby corrected as shown below:

Column 23, line 29, the formula portion should appear as follows:

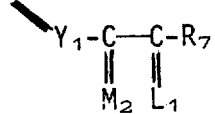

Column 23, line 40, the formula portion should appear as follows:

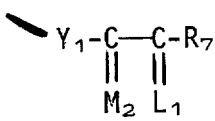

Column 23, line 50, the formula portion should appear as follows:

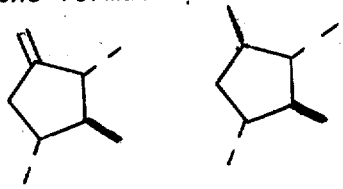

Column 23, line 58, the formula portions should appear as follows:

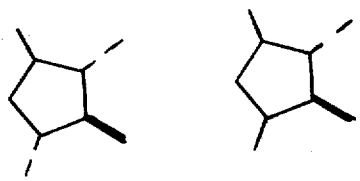

Column 23, line 67, the formula portions should appear as follows:

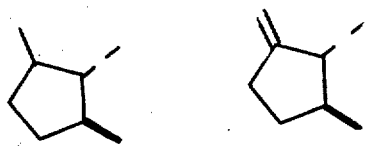

UNITED STATES PATENT OFFICE
CERTIFICATE OF CORRECTION

Patent No. 4,292,445     Dated 29 September 1981

Inventor(s) Norman A. Nelson

It is certified that error appears in the above-identified patent and that said Letters Patent are hereby corrected as shown below:

Column 24, line 68, "(8) $-(CH_2)_3-O-(CH_2)_{107}-$," should read -- (8) $-(CH_2)_3-O-(CH_2)-$, --.

Column 26, line 25, "wherein $R_7$ is" should read -- wherein $R_{17}$ is --.

Signed and Sealed this

*Twenty-eighth* Day of *December 1982*

[SEAL]

*Attest:*

GERALD J. MOSSINGHOFF

*Attesting Officer*     *Commissioner of Patents and Trademarks*